(12) United States Patent
Mateu et al.

(10) Patent No.: US 8,722,024 B2
(45) Date of Patent: May 13, 2014

(54) ESTER GELS, METHODS OF MANUFACTURE, AND USES THEREOF

(75) Inventors: Juan Mateu, Oak Ridge, NJ (US); Adam Perle, Saddle River, NJ (US)

(73) Assignee: Jeen International Corporation, Fairfield, NJ (US)

( * ) Notice: Subject to any disclaimer, the term of this patent is extended or adjusted under 35 U.S.C. 154(b) by 0 days.

(21) Appl. No.: 13/256,019

(22) PCT Filed: Mar. 12, 2010

(86) PCT No.: PCT/US2010/027128
§ 371 (c)(1),
(2), (4) Date: Sep. 12, 2011

(87) PCT Pub. No.: WO2010/105149
PCT Pub. Date: Sep. 16, 2010

(65) Prior Publication Data
US 2012/0003165 A1   Jan. 5, 2012

Related U.S. Application Data

(60) Provisional application No. 61/159,686, filed on Mar. 12, 2009.

(51) Int. Cl.
*A61K 8/92* (2006.01)

(52) U.S. Cl.
USPC .............. 424/59; 424/400; 424/486; 514/944

(58) Field of Classification Search
None
See application file for complete search history.

(56) References Cited

U.S. PATENT DOCUMENTS

| | | | | |
|---|---|---|---|---|
| 3,210,248 | A | * | 10/1965 | Feldmann et al. ............ 514/170 |
| 6,682,749 | B1 | * | 1/2004 | Potechin et al. .............. 424/401 |
| 2007/0196309 | A1 | * | 8/2007 | Tarletsky et al. .......... 424/70.12 |
| 2007/0243143 | A1 | * | 10/2007 | Patil et al. ....................... 424/59 |

FOREIGN PATENT DOCUMENTS

WO   WO 2007/100689   *   9/2007

* cited by examiner

*Primary Examiner* — Kortney L Klinkel
*Assistant Examiner* — Alissa Prosser
(74) *Attorney, Agent, or Firm* — Louis C. Paul, Esq.

(57) ABSTRACT

Gels of isopropyl esters of fatty alcohols that include a dimethyl/methylhydrogensiloxane copolymer, a silanol-terminated PDMS or an ethenyl-terminated PDMS, and a hydride functional siloxane. Also provided are methods for making the gels and articles containing them.

12 Claims, No Drawings

ESTER GELS, METHODS OF MANUFACTURE, AND USES THEREOF

The present invention relates to novel ester gels, methods of manufacturing such gels, and products incorporating such gels. The ester gels include esters that are obtainable by reacting isopropyl alcohol and fatty acids, and the use of such clear gelled esters in topical skin care formulations (i.e., containing cosmetic and/or dermatologic active ingredients) as well as color cosmetic products (e.g., lipsticks, liquid and stick foundations, and mascaras).

Polydimethylsiloxane (PDMS) is polymeric organosilicon compound having the chemical formula $(H_3C)_3SiO[Si(CH_3)_2O]_nSi(CH_3)_3$ where n is the number of repeating units, $[SiO(CH_3)_2]$.

Bis-vinyldimethicone/Vinyl Dimethicone Copolymer is an article of commerce available from a number of suppliers, including Jeen International, under the JeeSilc tradename, including as Jeesilc PS-VHBF, Jeesilc PS-CMBF and Jeesilc PS-DMBF.

Dimethicone/Vinyl Dimethicone Crosspolymer is a crosslinked dimethyl/methylhydrogensiloxane copolymer crosslinked with vinyl dimethylpolysiloxane. It is formed by a hydrosilation reaction between a dimethyl/methylhydrogensiloxane and a vinyl-terminated PDMS by one of two processes.

In a first "solution process", the dimethyl/methylhydrogensiloxane copolymer is dissolved in a solvent selected from the group consisting of cyclomethicone, low-viscosity dimethicones and hydrocarbons, for example isododecane. The dimethyl/methylhydrogensiloxane copolymer is reacted in solution with the vinyl-terminated PDMS.

In a second "suspension process" an aqueous suspension of dimethyl/methylhydrogensiloxane copolymer and a silanol-terminated or ethenyl-terminated PDMS is formed. A catalyst, typically platinum, is added to the suspension. The reaction is completed by heating.

Silanol-terminated PDMS is an article of commerce available from a number of suppliers including Gelest and Dow Corning. It is also described in the literature as hydroxy end-blocked Polydimethylsiloxane and alpha-hydro-omega-hydroxypoly (dimethylsiloxane).

Ethenyl-terminated PDMS is an article of commerce available from a number of suppliers including Gelest and Dow Corning. More particularly, ethenyl-terminated PDMS is a siloxane having an alkylene group having terminal olefinic unsaturation. A preferred ethenyl-terminated PDMS is vinyl-terminated PDMS capped with one or two vinyl groups.

Hydride functional siloxanes have at least one, and preferably a plurality of Si—H bonds capable of participating in a hydrosilylation reaction. Non-limiting examples of hydride functional siloxanes suitable use for in the methods and compositions of matter of the present invention include hydride-terminated methylhydrogensiloxane/dimethylsiloxane copolymers, hydride-terminated polyphenyl-methylsiloxane, hydride-terminated polyphenyl-(dimethylhydrosiloxy) siloxane. Hydride-terminated methylhydrogensiloxane/dimethylsiloxane copolymers are widely-used articles of commerce and are available from numerous suppliers including Gelest.

Dimethicone Crosspolymer is a polymer formed by crosslinking dimethicone through a $C_3$-$C_{20}$ alkenyl group. More particularly, a dimethyl/methylhydrogensiloxane copolymer is reacted by the solvent process described above with an organic compound having one or two terminal alkenyl groups.

Dimethicone Crosspolymer-3 is an article of commerce. Grades of Dimethicone Crosspolymer-3 useful in the practice of the present invention are available from Jeen International under the Jeesilc tradename, including Jeesilc IDD, Jeesilc 35C and Jeesilc 3D5LV, and conforms to the general structure:

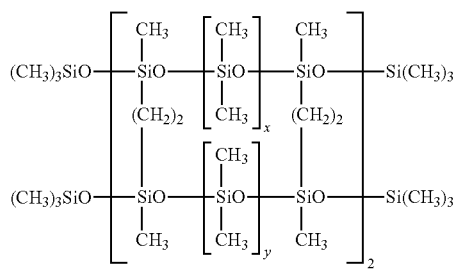

Polysilicone-11 is a crosslinked siloxane formed by the reaction of a ethenyl-terminated siloxane and methylhydroxydimethyl siloxane in the presence of cyclomethicone.

Dimethicone/Phenyldimethicone Crosspolymer is a copolymer of dimethylpolysiloxane crosslinked with phenyl vinyl dimethylpolysiloxane.

In a first aspect, the present invention provides a gelled ester made by the process of (i) combining a dimethicone/ethenyl dimethicone copolymer, preferably a dimethicone/vinyl dimethicone copolymer, with an ester obtainable by the reaction of isopropyl alcohol with a $C_2$-$C_{30}$ fatty acid to form a mixture, (ii) combining said mixture with either a silanol-terminated PDMS or an ethenyl-terminated PDMS, preferably a vinyl-terminated PDMS, in the presence of a catalyst, preferably platinum and the ester, The resulting product offers superiority over Dimethicone/Vinyl Dimethicone Crosspolymers made by the solvent process as described above (i.e., using cyclomethicone, low viscosity dimethicones and volatile hydrocarbons) that are currently available on the market. For example, the resulting product has a superior ability to absorb or imbibe silicones and organics. First, the novel gelled esters of the present invention is made without the use of volatile fluids or volatile organic solvents ("VOCs"). This helps to eliminate or minimize regulatory concerns (i.e., health and environmental) of certain finished goods companies who are, or plan to, reduce and/or phase out volatile fluids as raw materials. Moreover, eliminating volatile fluid raw materials provides finished goods companies with a wider array of packaging and transportation options. In contrast to one widely-used volatile fluid, isododecane, the novel agents of the present invention, do not defat the skin or leave an aesthetically undesirable whitening on the skin surface (i.e., after the isododecane has volatilized).

In a second aspect, the present invention provides a method for gelling a clear ester obtainable by the reaction of isopropyl alcohol with a $C_2$-$C_{30}$ fatty acid by combining the ester with (i) an agent formed by the reaction of dimethyl/methylhydrogensiloxane copolymer with (a) silanol-terminated PDMS and/or (b) ethenyl-terminated PDMS and (ii) a hydride functional siloxane. The thickening of the ester occurs after the addition of a catalyst, which is selected from the group consisting of platinum and tin.

For purposes of the present application, "clear" is understood to mean a color value of 1 or less on the Gardner Color Scale (ASTM D1544 "Standard Test Method for Color of Transparent Liquids (Gardner Color Scale)."

In a third aspect, the present invention provides a method for thickening an ester that can be obtained by the reaction of isopropyl alcohol with a $C_2$-$C_{30}$ fatty acid by combining the ester, preferably a $C_{12}$-$C_{22}$ fatty acid with, in sequence,
  (i) a gelling agent having reactive silane groups selected from the group consisting of Dimethicone/Vinyl Dimethicone Crosspolymer, Dimethicone Crosspolymer, Dimethicone Crosspolymer-3, Polysilicone-11, and Dimethicone/Phenyldimethicone Crosspolymer, and mixtures thereof; and
  (ii) a hydride functional siloxane; and
  (iii) a catalyst.

In a fourth aspect, the present invention provides a method for thickening an ester formed from the reaction of isopropyl alcohol with a $C_2$-$C_{30}$ fatty acid by combining the ester with;
  (i) a non-cross-linked silicone polymer made by the hydrosilylation reaction of a terminal divinyl silicone polymer and a hydride functional siloxane having silane reactive sites, for example a terminal disilanic-hydrogen silicone polymer; and
  (ii) a catalyst.

The non-cross-linked silicone polymer (INCI Name: Bis-vinyldimethicone/Dimethicone Copolymer) is more particularly described in international patent application publication WO/2007/100689 and U.S. Pat. No. 7,407,666, the disclosure of the latter is incorporated herein by reference in its entirety, and is sold under the tradename Jeesilc by Jeen International, including as Jeesilc PS-VHBF, Jeesilc PS-CMBF, Jeesilc PS-DMBF, PS-VHLV, Jeesilc PS-CMLV, Jeesilc PS-DMLV.

In a preferred embodiment of this aspect of the invention, volatile fluid (e.g., cyclomethicone, low viscosity dimethicone or isododecane) present from the formation of the non-cross-linked silicone polymer (made by the hydrosilylation reaction of a terminal divinyl silicone polymer and a terminal disilanic-hydrogen silicone polymer) is substantially removed prior to the reaction of the non-cross-linked silicone polymer with a hydride functional siloxane in the presence of a catalyst. By "substantially removed" is meant that less than 1%, preferably less than 0.5% and still more preferably less than 0.1% of volatile fluid.

In a fifth aspect, the present application provides a transfer-resistant and/or long-wear colored cosmetic products that include an ester thickened according to methods of the second and fourth aspects of the present invention. Preferably, the transfer-resistant and/or long-wear colored cosmetic product is further comprised of a thickener.

One preferred thickener is clay, non-limiting examples of which are bentonite, hectorite, kaolin and montmorillonite. Particularly preferred clay thickeners are disteardimonium hectorite and trialkylaryl ammonium hectorite, both organo-modified hectorites sold under the respective tradenames, Bentone 38V and Bentone 27V, by Rheox.

Other thickeners include trihydroxystearin (a triester of glycerin and hydroxystearic acid), olefin/styrene copolymers, such as Versagel M and Versagel MC (both from Penreco), propylene carbonate, synthetic layered magnesium silicate and synthetic layered fluorosilicates (both available under the Laponite tradename from Rockwood Additives Ltd), and magnesium aluminum silicates.

As will be appreciated by persons having ordinary skill in the art, certain ingredients disclosed herein as suitable for using in compositions containing the gelled esters of the present invention, including, for example, the hectorites listed above, may be dispersed in isododecane, isohexadecane, cyclomethicone, castor oil, sunflower oil, esters, petroleum distillates, mineral oil, phenyl trimethicone, caprylic/capric triglyceride, and may be sold in the form of such dispersions.

Tests for transfer-resistance are known to those of skill in the art and include the "Kiss Test" described in Example 4 of U.S. Pat. No. 5,505,937, the disclosure of which is incorporated herein by reference.

In a sixth aspect, the present application provides a long-wear personal care or skincare product that includes an ester thickened according to method of the second or fourth aspects of the present invention.

In one embodiment of this sixth aspect of the invention, the long-wear personal care product includes one or more active ingredients that block and/or attenuate ultraviolet radiation from 280-400 nm. In the United States, the use of sunscreens and sunblocks are regulated by the U.S. Food and Drug Administration. Accordingly, combinations of the following FDA-approved sunscreens and sunblocks may be used in long-wear personal care products of this aspect of the invention: p-Aminobenzoic acid up to 15%; Avobenzone up to 3%; Cinoxate up to 3%; Dioxybenzone up to 3%; Homosalate up to 15%; Menthyl anthranilate up to 5%; Octocrylene up to 10%; Octylmethoxycinnamate (Octinoxate) up to 7.5%; Octyl salicylate up to 5%; Oxybenzone up to 6%; Padimate 0 up to 8%; Phenylbenzimidazole sulfonic acid (Ensulizole) up to 4%; Sulisobenzone up to 10%; Titanium dioxide up to 25%; Trolamine salicylate up to 12%; Zinc oxide up to 25%. Other sunscreens and sunblocks approved in countries outside the U.S. are also suitable for inclusion in long-wear personal care products according to this aspect of the invention.

In another embodiment of this sixth aspect of the invention the long-wear skincare product is comprised of one or more skin care active ingredients that: (i) help to reduce the appearance of and/or prevent the formation of fine lines, wrinkles, age spots, sallowness, blotchiness, redness, dark circles (i.e., under the eyes); (ii) help to reduce skin oiliness; (iii) reduce transepidermal water loss; (iv) improve skin retention of moisture; and/or (v) improve skin elasticity. Non-limiting examples of such skincare actives include: anti-inflammatory agents (e.g., 1,3 1,6 beta glucan; polyglutamic acid (and) polyfructose); humectants; skin bleaching/lightening agents (e.g., hydroquinone, kojic acid, ascorbic acid, magnesium ascorbyl phosphate, ascorbyl 3 aminopropyl phosphate, ascorbyl 3 aminopropyl dihydrogen phosphate); skin soothing agents (e.g., panthenol and derivatives, aloe vera, pantothenic acid and its derivatives, allantoin, bisabolol, and dipotassium glycyrrhizinate); antioxidants; vitamins and derivatives thereof; exfoliants (e.g., abrasive particles, hydroxy-acids); anti-aging ingredients, including short-chain peptides, (i.e., having less than about 12 amino acids), including lipopeptides; and self-tanning agents (e.g., dihydroxyacetone).

Additional examples of skincare actives include antimicrobial agents and anti-acne agents (e.g., resorcinol, sulfur, salicylic acid, benzoyl peroxide, lincomycins), are disclosed in U.S. Pat. Nos. 6,492,326 and 6,277,892 and U.S. Patent Application Publication Nos. 2005/0142095 and 2004/0180020.

Compositions that include esters gelled in accordance with the present invention can also contain one or more of the following ingredients: (i) water-immiscible materials selected from the group consisting of volatile silicones, volatile paraffinic hydrocarbons, non-volatile silicones, non-volatile paraffinic hydrocarbons, cosmetically-acceptable esters, lanolin and derivatives thereof, glyceryl esters of fatty acids or triglycerides, fluorinated oils and Guerbet esters; (ii) film forming polymers, including silicone-containing and non-silicone polymers, the latter comprised of polymerized ethylenically unsaturated monomers either alone or in combination with one or more organic moieties; (iii) plasticizers in an amount sufficient to improve spreadability and application of the composition; (iv) viscosity modifiers.

Reduction in the appearance of fine lines and wrinkles can be measured by a number of techniques known to those of skill in the art and including clinical assessment by a trained observer (e.g., doctor, nurse, or technician) or by biophysical instrument (e.g., by use of Silflo replica masks) or an imaging system such as VISIA® from Canfield Scientific. Improvements in elasticity are measurable, for example, with a Twistometer. Reduction in the rate of transepidermal water loss and improvement in skin moisture content are measurable, respectively, with an evaporimeter and corneometer.

A seventh aspect of the present application, relates to anhydrous compositions for the delivery of L-ascorbic acid in which L-ascorbic acid is added to a composition comprising an ester thickened according to method of the second or fourth aspects of the present invention. L-ascorbic acid may be incorporated into anhydrous compositions of this aspect of the present invention at concentrations of from about 0.01 to about 20% by weight of the composition, preferably from 0.1 to 10% by weight. L-ascorbic acid may be incorporated into anhydrous compositions in pure form or dispersed in dimethiconol or a dimethiconol blend (i.e., in cyclomethicone, low viscosity dimethicone, petroleum distillate or esters). Examples of commercially-available dimethiconol blends include DC 1501 and 1503, both from Dow Corning.

The following examples are further illustrative of the present invention. The components and specific ingredients are presented as being typical, and various modifications can be derived in view of the foregoing disclosure within the scope of the invention.

EXAMPLE 1

Clear Gelled Ester ("CGE")

| Ingredient | | |
|---|---|---|
| Cyclomethicones and Dimethylsiloxanes (silanol-terminated dimethylsiloxane comprises from about 10%-15% by weight of the cyclomethicone/dimethylsiloxane blend; available from Jeen International as Jeesilc DMC 151) | 41.4 | 19.1 |
| Bis-vinyldimethicone/Dimethicone Copolymer (available from Jeen International as Jeesilc PS-DMLV) | 25.9 | 2.5 |
| Isopropyl Palmitate (Isopropryl Myristate and Isopropyl Isosterate may be substituted for Isopropyl Palmitate) | 5.2 | 66.0 |
| Methylhydrosiloxane/dimethylsiloxane copolymer, hydride-terminated | 10.4 | 6.2 |
| Platinum-divinyltetramethyl-disilazane complex in vinyl silicone solution (contains 3-3.5% platinum) | 17.1 | 6.2 |

Mix all ingredients (except platinum catalyst) until uniform. Add catalyst and mix. The resulting gel has a clear appearance (less than 1 on the Gardner color scale.). The product is referred to as "CGE" in the following examples.

EXAMPLE 2

Matte Foundation

| Ingredient | INCI Name | Supplier | % |
|---|---|---|---|
| PERMETHYL® 99A | Isododecane | Presperse | 21.00 |

-continued

| Ingredient | INCI Name | Supplier | % |
|---|---|---|---|
| CGE | [Isopropyl Palmitate and Bis-Vinyl Dimethicone/Dimethicone Copolymer] | Jeen Int'l | 9.00 |
| JEESILC® 110 | Dimethicone | Jeen Int'l | 3.00 |
| ABIL® EM-97 | Bis-PEG/PPG-14/14 Dimethicone & Cyclopentasiloxane | Degussa | 3.00 |
| JEECIDE® CAP-5 | Phenoxyethanol & Caprylyl Glycol & Potassium Sorbate & Water & Hexylene Glycol | Jeen Int'l | 1.00 |
| Yellow Iron Oxide SI | Iron Oxides & Methicone | Sensient/LCW | 1.00 |
| Red Iron Oxide SI | Iron Oxides & Methicone | Sensient/LCW | 0.20 |
| Black iron Oxide SI | Iron Oxides & Methicone | Sensient/LCW | 0.20 |
| GRANSIL® PSQ | Polymethylsilsesquioxane | Grant Ind. | 4.00 |
| Titanium Dioxide BTD-1152 | Titanium Dioxide & Triethoxycaprylylsilane | Kobo | 5.00 |
| Talc Micro Ace P-2 | Talc | Presperse | 3.00 |
| DI Water | Water | | 44.30 |
| KELTROL® CG | Xanthan Gum | | 0.30 |
| JEECHEM® BUGL | Butylene Glycol | Jeen Int'l | 4.00 |
| Sodium Chloride | Sodium Chloride | | 1.00 |

Using a homogenizer in the main tank, combine the PERMETHYL®, CGE and JEESILC® homogenize at a low speed. Add in the ABIL® EM-97 and JEECIDE® CAP-5 and mix for 15 minutes. Pre-blend the Iron Oxides and the other powders and mix in an Osterizer. Add to the main tank and homogenize at a medium speed until they are fully dispersed. In a side tank, add the water. Sprinkle in the KELTROL® and mix until fully dissolved. Add in the Butylene Glycol and Sodium Chloride. Slowly add the water phase to the oil phase using slow speed homogenizing agitation without aerating the batch. Mix for 20-25 minutes.

EXAMPLE 3

Lipstick

| Phase | Ingredient | INCI Name | Supplier | % |
|---|---|---|---|---|
| A | JEESILC® PDS-100 | Dimethicone | Jeen Int'l | 9.7 |
| A | JEESILC® PS-PTLV | Phenyl Trimethicone and Bis-Vinyl Dimethicone/Dimethicone Copolymer | Jeen Int'l | 10.0 |
| A | CGE | Isopropyl Palmitate and Bis-Vinyldimethicone/Dimethicone Copolymer (proposed) | Jeen Int'l | 20.0 |
| A | JEECHEM® TISC | Triisostearyl Citrate | Jeen Int'l | 2.5 |
| A | BENTONE® Gel IHDV | Isohexadecane and Distearyldimonium Hectorite and Propylene Carbonate | Elementis | 2.0 |
| A | JEESILC® CPS-312 | Cyclomethicone | Jeen Int'l | 40.8 |
| B | JEENATE® 4H | Polyethylene | Jeen Int'l | 5.0 |
| B | JEENATE® 5H | Polyethylene | Jeen Int'l | 9.0 |
| C | GANZPEARL® GPA-550 | Nylon 12 | Presperse Inc. | 1.00 |

Combine Phase A ingredients while heating at 85° C. Add Phase B ingredients to Phase A while heating at 85° C. Add Phase C ingredients to Phase A/B.

EXAMPLE 4

Concealer

| Tradename | INCI Name | | |
|---|---|---|---|
| PERMETHYL ® 99A | Isododecane | Presperse | 42.20 |
| CGE | [Isopropyl Palmitate Bis-Vinyldimethicone/Dimethicone Copolymer] | Jeen Int'l | 15.30 |
| JEENATE ® 4H | Polyethylene | Jeen Int'l | 5.10 |
| JEENATE ® 5H | Polyethylene | Jeen Int'l | 10.00 |
| TiO₂ SI | Titanium Dioxide and Methicone | LCW/Sensient | 15.00 |
| SPHERON ® L-1500 | Silica | Presperse Inc. | 5.00 |
| GANZPEARL ® GPA-550 | Nylon 12 | Presperse Inc. | 5.00 |
| Red Iron Oxide SI | Iron Oxide and Methicone | LCW/Sensient | 0.70 |
| Black Iron Oxide SI | Iron Oxide and Methicone | LCW/Sensient | 0.50 |
| Yellow Iron Oxide SI | Iron Oxide and Methicone | LCW/Sensient | 1.20 |

Blend iron oxides in an Osterizer and mix on high for 5 minutes. Add all oils and waxes to main tank and heat to 75-80° C. Add iron oxides to oils and waxes and homogenize until smooth.

EXAMPLE 5

Hand and Body Lotion

| Phase | Tradename | INCI Name | Supplier | % |
|---|---|---|---|---|
| A | Deionized Water | Water | | 77.0 |
| A | ULTREZ ® 10 | Carbomer | Noveon | 0.40 |
| B | Stearic Acid | Stearic Acid | Jeen Int'l | 3.50 |
| B | Cetyl Alcohol | Cetyl Alcohol | Jeen Int'l | 1.00 |
| B | Stearyl Alcohol | Stearyl Alcohol | Jeen Int'l | 1.50 |
| B | JEECHEM ® TN | C12-15 Alkyl Benzoate | Jeen Int'l | 7.00 |
| B | JEESORB ® O-20 | Polysorbate 80 | Jeen Int'l | 0.50 |
| C | TEA 99% | Triethanolamine | Jeen Int'l | 0.60 |
| D | JEECIDE ® CAP-5 | Phenoxyethanol & Caprylyl Glycol & Potassium Sorbate & Water & Hexylene Glycol | Jeen Int'l | 1.00 |
| D | Vitamin E Acetate | Tocopheryl Acetate | Jeen Int'l | 0.50 |
| D | JEECHEM ® FS-102 | Hexylene Glycol & PEG-25 Hydrogenated Castor Oil & PEG-40 Hydrogenated Castor Oil | Jeen Int'l | 1.00 |
| D | Fragrance | Fragrance | | 0.50 |
| E | CGE | Isopropyl Palmitate and Bis-Vinyl Dimethicone/Dimethicone Copolymer | Jeen Int'l | 4.00 |
| F | Algae Extract | Algae Extract | Botanicals Plus | 1.5 |
| G | FD&C Blue #1 | | | Q.S. |

Add D.I. Water and sprinkle in ULTREZ® 10 using propeller mixing. Heat Phase A to 70° C. Add Phase B ingredients one at a time to the batch and maintain 70° C. Switch to sweep agitation and add Phase C. Mix well. Pre-mix Phase D in a side vessel. Cool batch to 50-55° C. and add pre-mix Phase D. Add Phase E and mix well. Add Phase F. Add Phase G. Cool batch to room temperature.

What is claimed is:

1. A clear gelled isopropyl ester of a C2-C20 fatty acid prepared by the process of reacting a bis-vinyldimethicone/dimethicone copolymer with (i) either a silanol-terminated PDMS or an ethenyl-terminated PDMS and (ii) a hydride functional siloxane in the presence of the isopropyl ester of a C2-C20 fatty acid and a catalyst comprising platinum or tin to obtain the clear gelled ester.

2. A composition comprising the clear gelled ester of claim 1 and further comprising at least one additional component selected from any one or more of the following groups: (i) water-immiscible materials selected from the group consisting of volatile silicones, volatile paraffinic hydrocarbons, non-volatile silicones, non-volatile paraffinic hydrocarbons, cosmetically-acceptable esters, lanolin and derivatives thereof, glyceryl esters of fatty acids or triglycerides, fluorinated oils and Guerbet esters; (ii) film forming polymers, including silicone-containing and non-silicone polymers, the latter comprised of polymerized ethylenically unsaturated monomers either alone or in combination with one or more organic moieties; (iii) plasticizers; and (iv) viscosity modifiers.

3. A composition comprising the clear gelled ester of claim 1 and further comprising at least one additional component selected from either or both the following groups: (i) water-immiscible materials selected from the group consisting of volatile silicones, volatile paraffinic hydrocarbons, non-volatile silicones, non-volatile paraffinic hydrocarbons, cosmetically-acceptable esters, lanolin and derivatives thereof, glyceryl esters of fatty acids or triglycerides, fluorinated oils and Guerbet esters; and (ii) film forming polymers, including silicone-containing and non-silicone polymers, the latter comprised of polymerized ethylenically unsaturated monomers either alone or in combination with one or more organic moieties.

4. A composition comprising the clear gelled ester of claim 1 and further comprising at least one sunscreen or sunblock.

5. The composition of claim 4 wherein the sunscreen or sunblock is selected from the group consisting of: p-aminobenzoic acid up to 15%; avobenzone up to 3%; cinoxate up to 3%; dioxybenzone up to 3%; homosalate up to 15%; menthyl anthranilate up to 5%; octocrylene up to 10%; octylmethoxycinnamate, up to 7.5%; octyl salicylate up to 5%; oxybenzone up to 6%; padimate-O up to 8%; phenylbenzimidazole sulfonic acid up to 4%; sulisobenzone up to 10%; titanium dioxide up to 25%; trolamine salicylate up to 12%; and zinc oxide up to 25% wherein all % are recited in percentage by weight.

6. A composition comprising the clear gelled ester of claim 1 and further comprising at least one skin care active ingredient selected from the group consisting of: anti-inflammatory agents, humectants, skin bleaching agents, a skin soothing agents, antioxidants, vitamins, exfoliants, anti-ageing compounds, antimicrobial agents, and anti-acne ingredients.

7. A method of thickening an isopropyl ester of a C2-C30 fatty acid, the method comprising the step of reacting: (i) a bis-vinyldimethicone/dimethicone copolymer, with (ii) either a silanol-terminated PDMS or an ethenyl-terminated PDMS, and (iii) a hydride functional siloxane, in the presence of (iv) a catalyst selected from the group consisting of platinum and tin and the ester.

8. The method of claim 7 wherein the ester and components (i), (ii), and (iii) are first combined to form a first combination, whereafter the catalyst is combined with the first combination.

9. The method of claim 7 wherein the hydride functional siloxane is a hydride-terminated methylhydrosiloxane/dimethylsiloxane copolymer.

10. The method of claim 9 wherein the hydride-terminated methylhydrosiloxane/dimethylsiloxane copolymer includes from about 15 to 50 mole percent of methylhydrosiloxane.

11. The method of claim 10 where the catalyst is platinum.

12. The method of claim 7 where the isopropyl ester of a C2-C30 fatty acid is selected from the group consisting of isopropyl palmitate, isopropopyl myristate and isopropyl isostearate.

* * * * *